US008204582B2

(12) United States Patent  (10) Patent No.: US 8,204,582 B2
Zantos et al.  (45) Date of Patent: Jun. 19, 2012

(54) ADAPTIVE REAL TIME ECG TRIGGERING AND USES THEREOF

(75) Inventors: George N. Zantos, Medford, MA (US); Patricia Hanlon-Pena, Kingwood, TX (US)

(73) Assignee: Arrow International, Inc., Reading, PA (US)

( * ) Notice: Subject to any disclaimer, the term of this patent is extended or adjusted under 35 U.S.C. 154(b) by 1016 days.

(21) Appl. No.: 11/634,687

(22) Filed: Dec. 6, 2006

(65) Prior Publication Data

US 2007/0161916 A1   Jul. 12, 2007

Related U.S. Application Data

(60) Provisional application No. 60/758,962, filed on Jan. 12, 2006.

(51) Int. Cl.
 *A61B 5/0456* (2006.01)
(52) U.S. Cl. ......... 600/521; 600/508; 600/509; 600/547
(58) Field of Classification Search .......... 600/508–509, 600/521, 547
See application file for complete search history.

(56) References Cited

U.S. PATENT DOCUMENTS

| 4,571,547 | A | | 2/1986 | Day |
| 4,617,938 | A | * | 10/1986 | Shimoni et al. ............... 600/521 |
| 4,692,148 | A | | 9/1987 | Kantrowitz et al. |
| 4,809,681 | A | | 3/1989 | Kantrowitz et al. |
| 5,355,891 | A | | 10/1994 | Wateridge et al. |
| 5,365,932 | A | * | 11/1994 | Greenhut ..................... 600/508 |
| 5,913,814 | A | | 6/1999 | Zantos |
| 6,070,097 | A | * | 5/2000 | Kreger et al. ................. 600/521 |
| 6,258,035 | B1 | | 7/2001 | Hoeksel et al. |
| 6,290,641 | B1 | | 9/2001 | Nigroni et al. |
| 6,569,103 | B2 | | 5/2003 | Hoeksel et al. |
| 6,679,829 | B2 | * | 1/2004 | Nigroni et al. ................. 600/18 |
| 6,887,206 | B2 | | 5/2005 | Hoeksel et al. |
| 7,090,644 | B2 | | 8/2006 | Hoeksel et al. |
| 139,605 | A1 | | 11/2006 | Gerasimov |
| 7,169,109 | B2 | | 1/2007 | Jansen et al. |
| 7,283,870 | B2 | * | 10/2007 | Kaiser et al. ................. 600/547 |
| 2002/0010402 | A1 | | 1/2002 | Hoeksel et al. |
| 2004/0186388 | A1 | | 9/2004 | Gerasimov |
| 2005/0148812 | A1 | | 7/2005 | Nigroni et al. |

OTHER PUBLICATIONS

"PCT Notification Concerning Transmittal of International Preliminary Report on Patentability" dated Dec. 11, 2008 issued by the International Bureau of WIPO in connection with PCT/US2006/046441. (7 pages).

Minich L et al., "Neonatal Piglet Model of Intra-Aortic Balloon Pumping: Improved Efficacy Using Echocardiographic Timing," Annals of Thoracic Surgery, 1998; 66, pp. 1527-1532.

Elghazzawi Z F et al., "Algorithm to Identify Components of Arterial Blood Pressure Signals During Use of an Intra-Aortic Balloon Pump," Journal of Clinical Monitoring, vol. 9, No. 4, Sep. 1993, pp. 297-308.

(Continued)

*Primary Examiner* — Niketa Patel
*Assistant Examiner* — Rex R Holmes
(74) *Attorney, Agent, or Firm* — Baker & Hostetler LLP

(57) ABSTRACT

The present invention provides methods and apparatus for generating a trigger from the R wave of an electrocardiogram (ECG) waveform using a threshold that adapts to the slope of the R wave while still within the leading edge of the R wave.

44 Claims, 5 Drawing Sheets

OTHER PUBLICATIONS

Pantalos G M et al., "Estimation of Timing Errors for the Intraaortic Balloon Pump Use in Pediatric Patients," ASAIO Journal, 1999, 45(3); pp. 166-171.

Kern M J et al., "Hemodynamic effects of new intra-aortic balloon counterpulsation timing methods in patients: A multicenter evaluation," American Heart Journal, Jun. 1999, vol. 137, No. 6, pp. 1129-1136.

Sakamoto T et al., "New Algorithm of Intra Aortic Balloon Pumping in Patients with Atrial Fibrillation," ASAIO Journal Jan.-Mar. 1995, vol. 41, No. 1, pp. 79-83.

Ohley W J et al., "Intraaortic balloon pump response to arrhythmias: Development and implementation of algorithms," Cardioangiology, May 2002, vol. 51, No. 5, pp. 483-487.

International Searching Authority, "Notification of Transmittal of the International Search Report and the Written Opinion of the International Searching Authority," for International Application No. PCT/US2006/046441, 9 pages.

Supplementary European Search Report from the European Patent Office dated Dec. 8, 2009 in connection with European Patent Application No. 06844852.1, 5 pages.

* cited by examiner

ADAPTIVE REAL TIME ECG TRIGGERING AND USES THEREOF

CROSS-REFERENCE TO RELATED APPLICATION

This application claims the benefit of U.S. Provisional Patent Application No. 60/758,962, filed Jan. 12, 2006, the content of which is incorporated by reference.

FIELD OF THE INVENTION

The present invention is directed to methods and apparatus for generating a trigger from the R wave of an electrocardiogram (ECG) waveform using a threshold that adapts to changes in slope of the leading edge of the R wave. The invention can be used, for example, to trigger an intra-aortic balloon pump (IABP) to control an intra-aortic balloon (IAB), to trigger an interactive cardiac device such as a cardiac stimulator or defibrillator, and as an ECG monitor.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

Subjects with poorly functioning hearts can have compromised blood supply to vital organs. The pumping action of the heart and the systemic blood supply can be improved by the use of an intra-aortic balloon pump (IABP) to control an intra-aortic balloon (IAB). IABPs are used in cardiology patients and cardiac surgery patients (Baskett et al., 2002; Mehlhorn et al., 1999).

In each cardiac cycle, the IAB is inflated by means of the pumping device after the end of the ejection phase of the left ventricle of the heart, and is deflated again before the commencement of the following ejection phase. It has been suggested that systemic hemodynamics and myocardial efficiency can be improved by balloon deflation approaching or simultaneous with left ventricular ejection (Kern et al., 1999). For optimal functioning of the IABP, it is important that the IAB be inflated and deflated at the correct times in the cardiac cycle.

Methods and apparatus for controlling the inflation of an IAB have been described, for example, in Sakamoto et al., 1995; U.S. Pat. Nos. 4,692,148, 6,258,035, 6,569,103 and 6,887,206; and U.S. patent application Publication Nos. 20040059183 and 20050148812.

Deflation of the IAB can be triggered using the electrocardiogram (ECG) of the subject's heart (e.g., Ohley et al., 2002; U.S. Pat. Nos. 4,692,148, 4,809,681, 6,290,641 and 6,679,829). Methods and apparatus for determining a trigger signal from an ECG have been described (e.g., U.S. Pat. Nos. 4,571,547 and 5,355,891). Typically, the timing of deflation of the IAB is based on the R Wave of the ECG. There is a need for accurate R wave triggering where the trigger adapts in real time to changes in R wave amplitude and rise time during the leading phase of the R wave.

SUMMARY OF THE INVENTION

The present invention satisfies this need by providing improved methods and apparatus for generating a trigger from the R wave of an electrocardiogram (ECG) waveform using a threshold that adapts to the slope of the R wave while still within the leading edge of the R wave.

The method comprises the steps of: a) setting a minimum threshold for the trigger, where the minimum threshold is a percentage of the amplitude of the expected R wave; b) measuring slopes of the R wave over successive small time periods during the leading edge of the R wave, where slopes corresponding to waveforms that consist of frequencies greater than the expected R wave prevent generation of a trigger; c) adjusting the threshold for the trigger for the R wave during the leading edge of the R wave, where the minimum threshold is increased if the slopes measured in b) are greater than expected for the R wave; d) applying a scalar value to the slopes measured in b) to set a frequency above which signal frequencies are not considered valid for recognition as an R wave; and e) generating a trigger within the leading edge of the R wave when the amplitude of the R wave reaches the threshold.

The apparatus of the present invention comprises a processing unit for: a) setting a minimum threshold for the trigger, where the minimum threshold is a percentage of the amplitude of the expected R wave; b) measuring slopes of the R wave over successive small time periods during the leading edge of the R wave, where slopes corresponding to waveforms that consist of frequencies greater than the expected R wave prevent generation of a trigger; c) adjusting the threshold for the trigger for the R wave during the leading edge of the R wave, where the minimum threshold is increased if the slopes measured in b) are greater than expected for the R wave; d) applying a scalar value to the slopes measured in b) to set a frequency above which signal frequencies are not considered valid for recognition as an R wave; and e) generating a trigger within the leading edge of the R wave when the amplitude of the R wave reaches the threshold.

The present invention advances the state of R wave triggering by providing real time triggering during the leading edge of the R wave with improved trigger recognition and reduced false triggers and missed triggers.

Additional objects of the invention will be apparent from the description which follows.

DETAILED DESCRIPTION OF THE INVENTION

Figure 1:
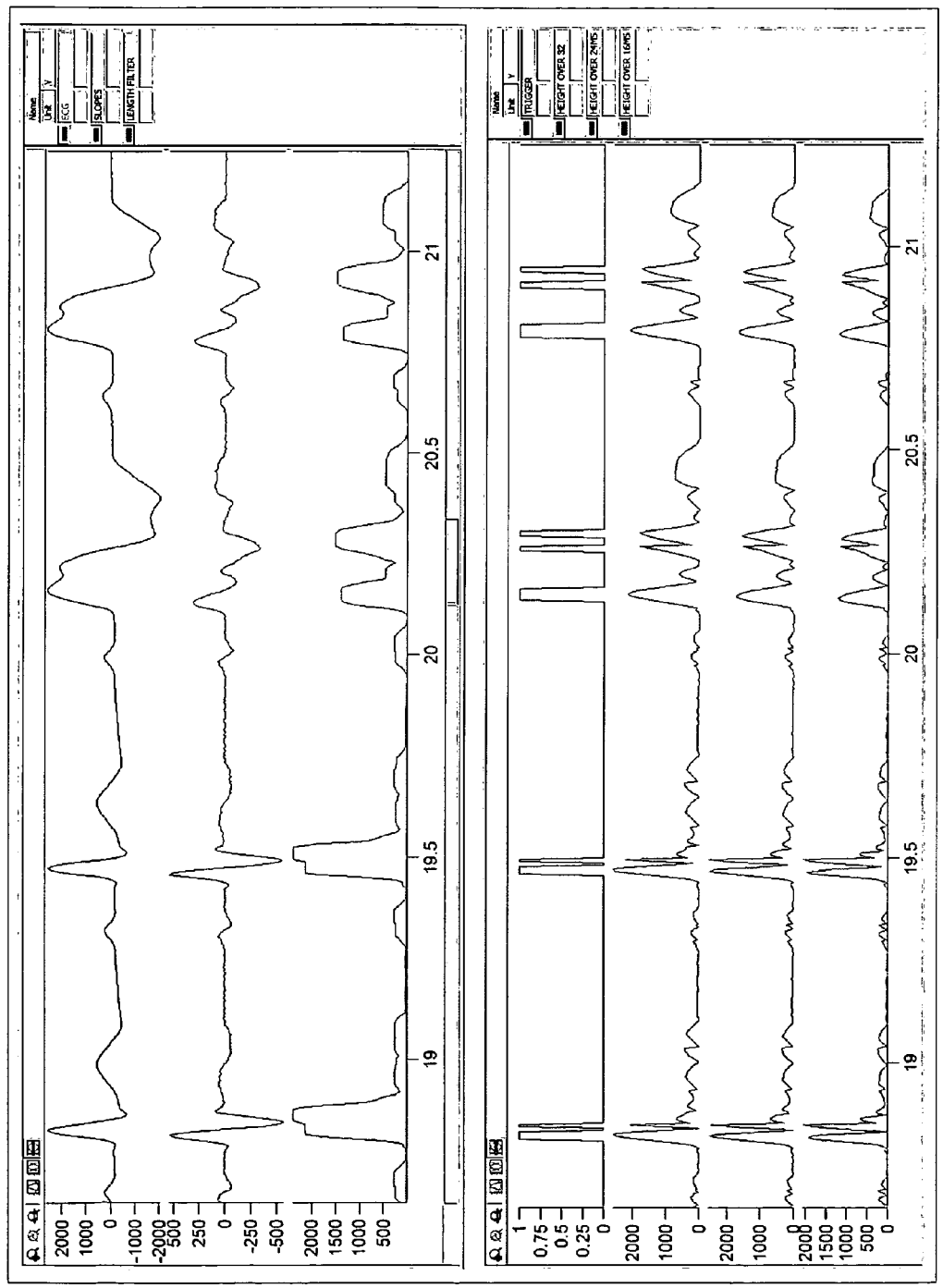
FIG. 1. R wave triggering during different ECG morphologies. Top panels in FIGS. 1-5 show, from top to bottom, simulated ECG, slope of ECG over 4 ms periods, and length filter or adaptive threshold for the R wave trigger. Bottom panels show, from top to bottom, occurrence of trigger, and ECG height over periods of 32 ms, 24 ms and 16 ms. The figure illustrates that the adaptive threshold can adjust the threshold for the R wave trigger during changes in R wave shape or morphology. The time scale on the X-axis of FIGS. 1-5 is in seconds.

The present invention is directed to methods and apparatus for generating a trigger from an R wave of an electrocardiogram (ECG) waveform using a threshold that adapts to the slope of the R wave while still within the leading edge of the R wave. The invention can be used in subjects with a normal cardiac rhythm. However, the invention is particularly useful in subjects who have cardiac arrhythmia because it allows earlier R wave recognition, during the leading edge of the R wave. The earlier an R wave is recognized during cardiac arrhythmia, the more time that is available to deflate an IAB before the next cardiac cycle. The invention may be used in the treatment of human subjects or in veterinary medicine.

The method of the present invention comprises the following steps a)-e). Step a) involves setting a minimum threshold for the trigger, where the minimum threshold is a percentage of the amplitude of the expected R wave. The R wave may represent an increase or a decrease in voltage from the ECG baseline depending on the polarity of the ECG signal that is recorded. Thus, the leading edge of the R wave may represent either a rise or fall from the baseline of the ECG. The amplitude of the expected R wave is typically normalized based on preceding R waves recorded from the same subject. More recently occurring R waves can be weighted more heavily in determining the amplitude of the expected R wave than less recently occurring R waves. The minimum threshold criteria is important to prevent falsely triggering on small amplitude artifacts or noise. The minimum threshold can be set, for example, at about ⅓ to about ½ of the amplitude of the expected R wave. Preferably, the minimum threshold is set at ⅓ of the amplitude of the expected R wave. The adaptive trigger threshold feature of the present invention allows a lower initial minimum threshold to be used to allow better detection of R waves with a slowly changing leading edge, while not increasing the false trigger rate.

Step b) involves measuring slopes of the R wave over successive small time periods during the leading edge of the R wave, where slopes corresponding to waveforms that consist of frequencies greater than the expected R wave prevent generation of a trigger. The individual time periods may be, for example, 1 msec to 5 msec in duration. Preferably, individual time periods are at least 4 msec in duration. The total duration of the successive time periods may be, for example, 16-40 msec. This step can involve using a weighted average of the observed slope, with the most recent values getting the most weight and successively less weight applied as the values gets older. This is a dynamic measurement and adjustment that solely relies on the values seen within the existing R wave and not on previous R waves. Preferably, slopes corresponding to waveforms that consist of frequencies greater than or equal to 30-40 Hz are excluded from generating a trigger. The method can further comprise excluding slopes corresponding to waveforms that consist of frequencies less than or equal to 5-10 Hz from generating a trigger.

Step c) involves adjusting the threshold for the trigger for the R wave during the leading edge of the R wave, where the minimum threshold is increased if the slopes measured in b) are greater than expected for the R wave. Preferably, the adjusted threshold is not allowed to exceed a maximum percentage of the amplitude of the expected R wave. More preferably, the adjusted threshold is not allowed to exceed $\frac{2}{3}^{rd}$ of the amplitude of the expected R wave. The minimum threshold criterion set in step a) is critical in that it allows time to sample several small increments of the leading edge of the R wave in order to adjust the threshold value before the minimum threshold value is exceeded.

Step d) involves applying a scalar value to the slopes measured in b) to set a frequency above which signal frequencies are not considered valid for recognition as an R wave. This feature further improves the recognition of the R wave. The scalar value can be applied using various mathematical operations. A preferred method comprises multiplying the slopes obtained in step b) by a frequency scalar value that determines the frequencies that are allowed to generate a trigger in step e). This will eliminate triggers based on frequencies greater than what the chosen scalar will allow, as illustrated in Table 1.

TABLE 1

Effects of frequency scalar on rejection of frequencies for ECG trigger detection. Frequencies in Hz.

| | Frequency Scalar | | | | | | |
|---|---|---|---|---|---|---|---|
| | 2 | 2.5 | 3 | 3.5 | 4 | 5 | 6 |
| Frequencies ≧ that are rejected | 70 | 48 | 40 | 32 | 28 | 22 | 18 |

Step e) involves generating a trigger within the leading edge of the R wave when the amplitude of the R wave reaches the threshold. The generated trigger may be used to trigger an intra-aortic balloon pump (IABP). In particular, the trigger may be used to trigger deflation of an intra-aortic balloon (IAB) by an intra-aortic balloon pump (IABP). In addition, the generated trigger can be used to trigger an interactive cardiac device such as a cardiac stimulator or defibrillator, and as an ECG monitor.

The invention also provides apparatus for generating a trigger from an R wave of an electrocardiogram (ECG) waveform using a threshold that adapts to the slope of the R wave while still within the leading edge of the R wave, where the apparatus comprises a processing unit for:
  a) setting a minimum threshold for the trigger, where the minimum threshold is a percentage of the amplitude of the expected R wave;
  b) measuring slopes of the R wave over successive small time periods during the leading edge of the R wave, where slopes corresponding to waveforms that consist of frequencies greater than the expected R wave prevent generation of a trigger;
  c) adjusting the threshold for the trigger for the R wave during the leading edge of the R wave, where the minimum threshold is increased if the slopes measured in b) are greater than expected for the R wave;
  d) applying a scalar value to the slopes measured in b) to set a frequency above which signal frequencies are not considered valid for recognition as an R wave; and
  e) generating a trigger within the leading edge of the R wave when the amplitude of the R wave reaches the threshold.

Preferably, the apparatus also includes inputs from the subject's electrocardiogram (ECG) and from the subject's arterial pressure (AP), and a processing unit for detecting cardiac arrhythmia in the subject from the subject's electrocardiogram (ECG) and/or from the subject's arterial pressure. Preferably, the apparatus also includes an output that triggers an IABP, in particular deflation of the IAB. The apparatus can be incorporated in an intra-aortic balloon pump console system. The apparatus can include an output that triggers an interactive cardiac device such as a cardiac stimulator or defibrillator, and/or an output to an ECG monitor.

The method or processing unit can further comprise requiring that a minimum number of changes in amplitude of the R wave measured over successive time periods in step b) are in the same direction of change in order to generate a trigger. Requiring a minimum number of segments moving in the same direction helps to rule out a trigger on frequencies higher than the expected R wave. This check is done starting with the first time period of the leading edge of the R wave to pre-validate the trigger so as not to impose any delay in issuing the trigger once the amplitude criteria are satisfied.

The method or processing unit can further comprise requiring that a change in amplitude of the R wave measured over an individual time period in step b) has a minimum change with respect to the change in amplitude measured for the preceding time period in order for a trigger to be generated.

The method or processing unit can further comprise increasing the threshold for the trigger in the presence of ECG signals having a frequency component in the higher range expected for the R wave. The ECG normally has a frequency range of about 10 to 30 Hz. The threshold for the trigger can be increased, for example, in the presence of ECG signals having a 25-30 Hz frequency component. For example, the threshold for the trigger of an R wave can be increased in the presence of signals that are consistent with frequencies of an R wave such that noise that is less than $\frac{2}{3}^{rd}$ of the threshold is excluded from being falsely called an R wave, but the true R wave is still recognized if and when it exceeds the threshold. This can be achieved by setting the frequency scalar multiplier to a value such that it is within the upper range of expected R wave.

Another refinement is to have the ECG waveform normalized in amplitude, such that the amplitude of the ECG is gained to achieve a target value. This allows for a fixed set of thresholds for triggering and filter coefficients that would not have to be scaled for the strength of the signal received.

The time period during which the threshold is checked for a trigger can be specified. For example, the time period can be a limited time period, for example a time period of 16 to 40 ms. The threshold for the trigger can also be checked looking back, for example, at 16, 20, 24, 28, 32 and 40 ms intervals. These specified time intervals help define the frequencies that are allowed to generate a trigger.

The method or processing unit further provides that after a trigger is generated in step e), a second trigger cannot be generated within a specified time period. This time period may be set, for example, at around 280 ms.

The present invention is illustrated in the following Experimental Details section, which is set forth to aid in the understanding of the invention, and should not be construed to limit in any way the scope of the invention as defined in the claims that follow thereafter.

EXPERIMENTAL DETAILS

Problem to be Solved

A problem existed in recognizing the various morphologies that can occur for the QRS segment of an ECG. The goal is to reliably trigger on the leading edge of the R wave in real time. The ECG normally has a frequency range of 10 to 30 Hz.

The R wave of the ECG can have slopes and rise times that differ by a factor of 5 or more. The leading edge of the R wave can have a rise time from 16 msec to 100 msec. Trigger thresholds set to detect the slowest R waves may also end up detecting ECG T waves and P waves in the faster ECG morphologies. Thus, there is the need to have an adaptive trigger threshold that adjusts in real time for differing ECG morphologies.

One purpose of the present invention is to prevent triggering on a signal that has frequencies above the normal range that would otherwise have sufficient slope and amplitude to be considered the leading edge of the R wave. A further purpose of the invention is based on the need to recognize the leading edge of the ECG R wave as soon as possible, so that the IABP can determine when the next cardiac cycle is taking place. This requirement does not allow for traditional filtering techniques that cause a significant propagation delay in the signal and result in late recognition of the start of the R wave.

Results and Discussion

The present invention was incorporated into a currently used IABP device (Arrow International AUTOCAT® version 2.22). In testing against a subset of the American Heart Association (AHA) ECG database (42 tapes), the following improvements in R wave triggering were obtained with the present invention compared to the version of the IABP without the present invention. The percentage of missed triggers was reduced 40% and the percentage of false triggers was reduced 90%. Thus, the present invention provides better detection of a wide range of R waves while at the same time reducing the incidence of false detection.

Figure 2:
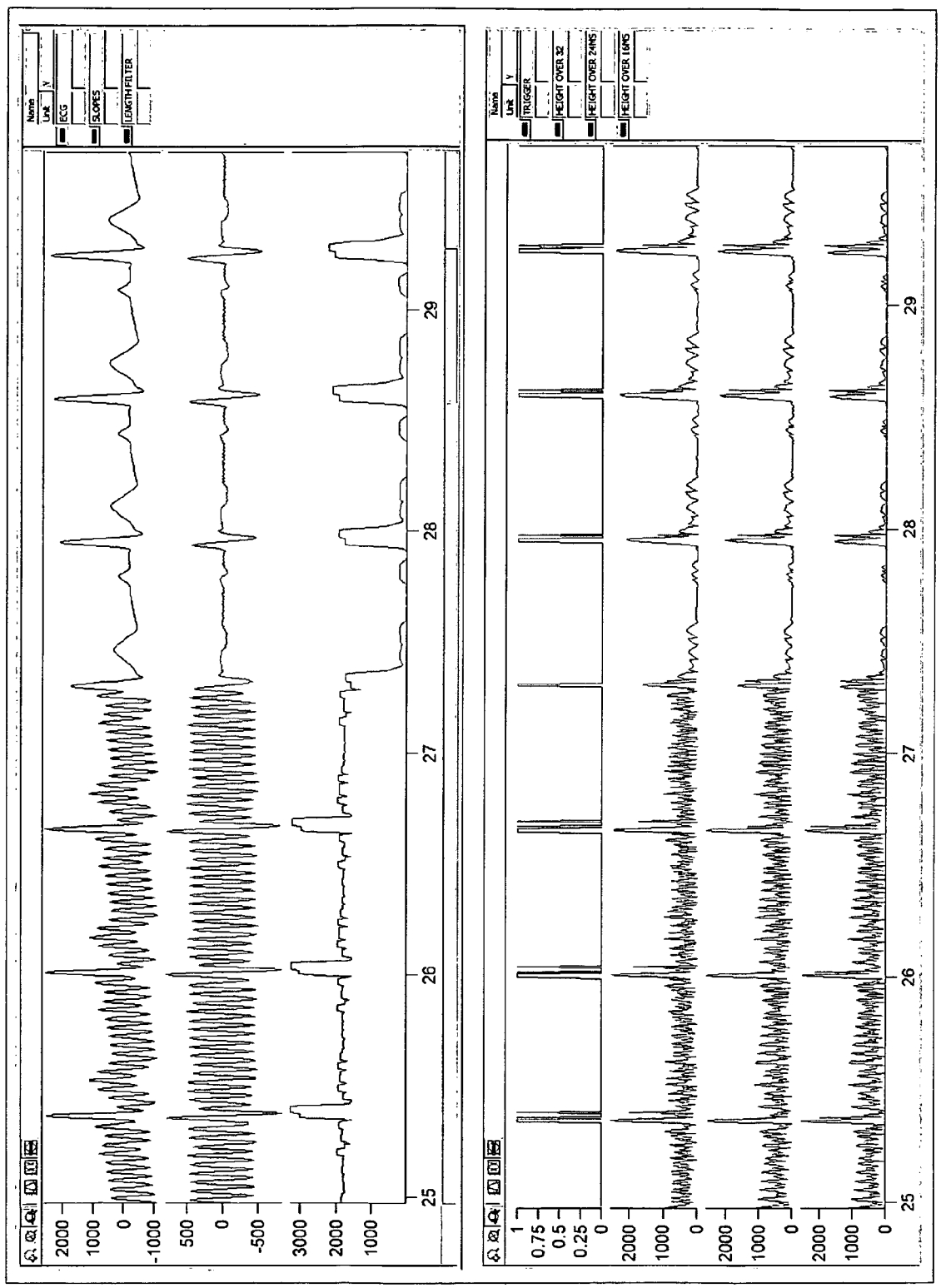
FIG. 2. R wave triggering during changes in noise level. The figure illustrates how the threshold for R wave triggering quickly adapts to changes in the noise level on the ECG signal. The time period over which the ECG height is checked (bottom panel) prevents signal frequencies higher than expected for the R wave from meeting the trigger criteria.
Figure 3:
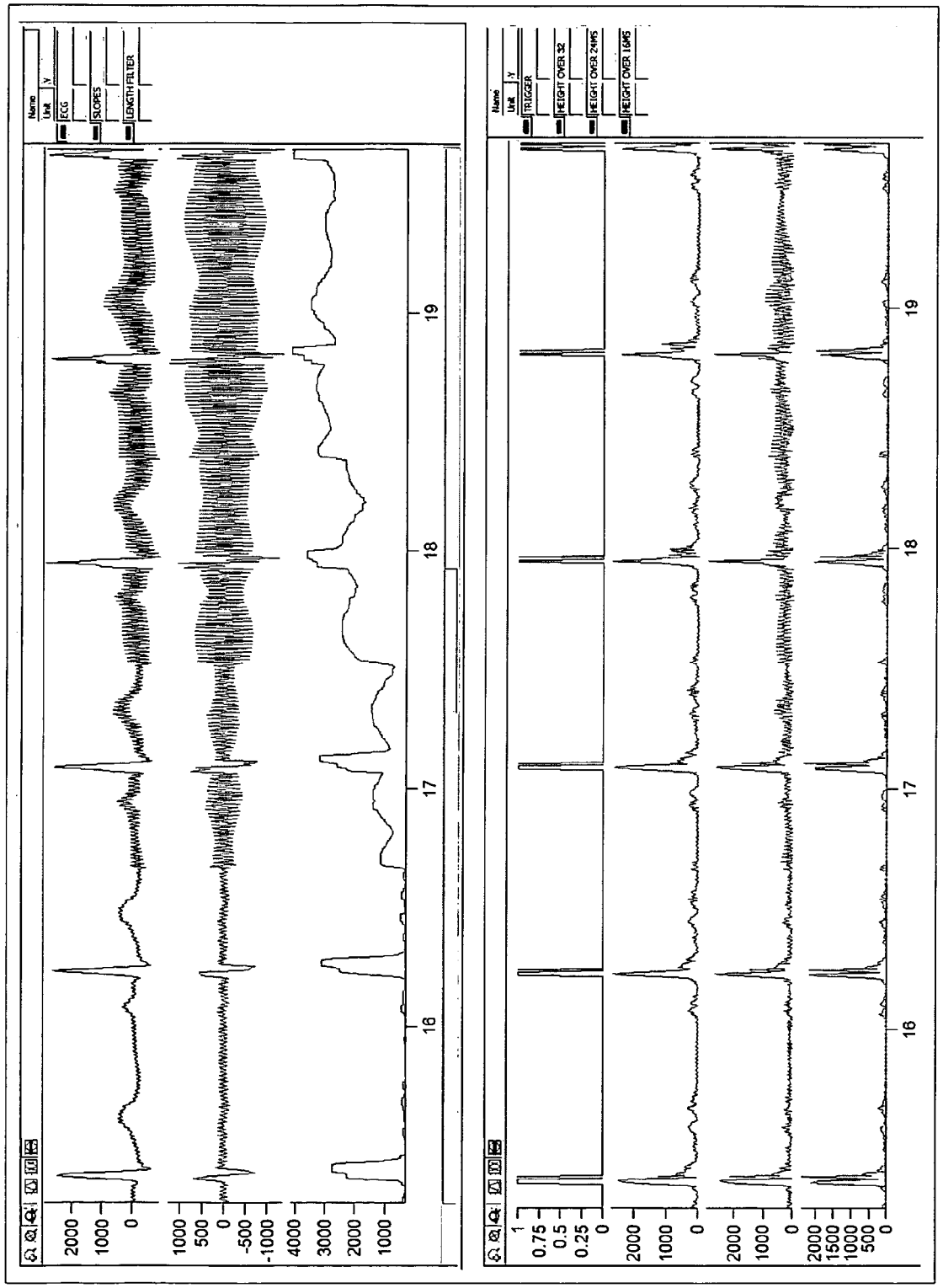
FIG. 3. R wave triggering during introduction of 60 cycle noise on ECG. The threshold actively adapts to the 60 cycle noise by increasing the threshold level during real time. The time period over which the ECG height is checked prevents frequencies outside of the range of the R wave from generating a trigger.
Figure 4:
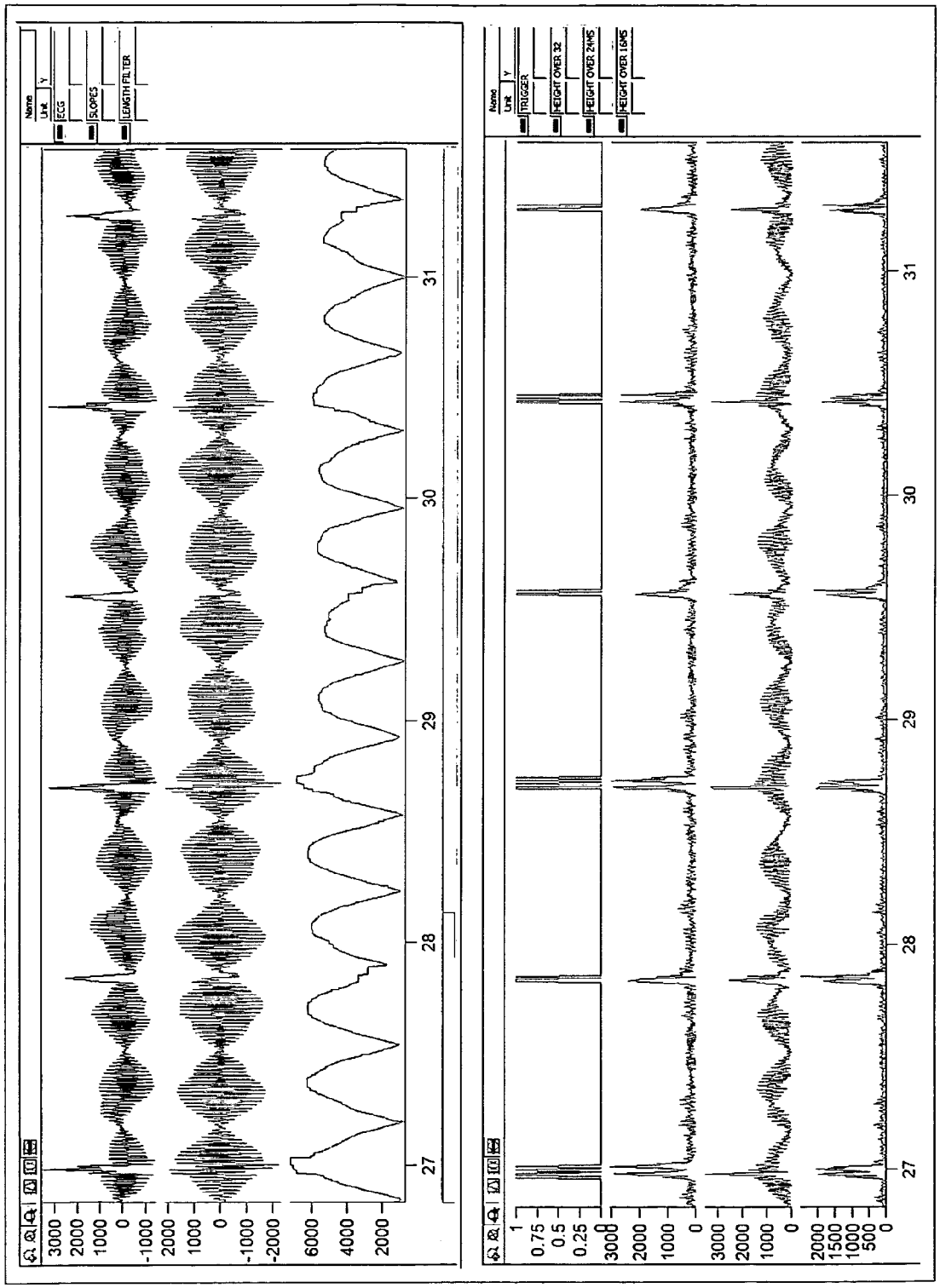
FIG. 4. R wave triggering during modulated 60 cycle noise on ECG. The threshold rapidly adapts to changes in the amplitude of the 60 cycle noise.
Figure 5:
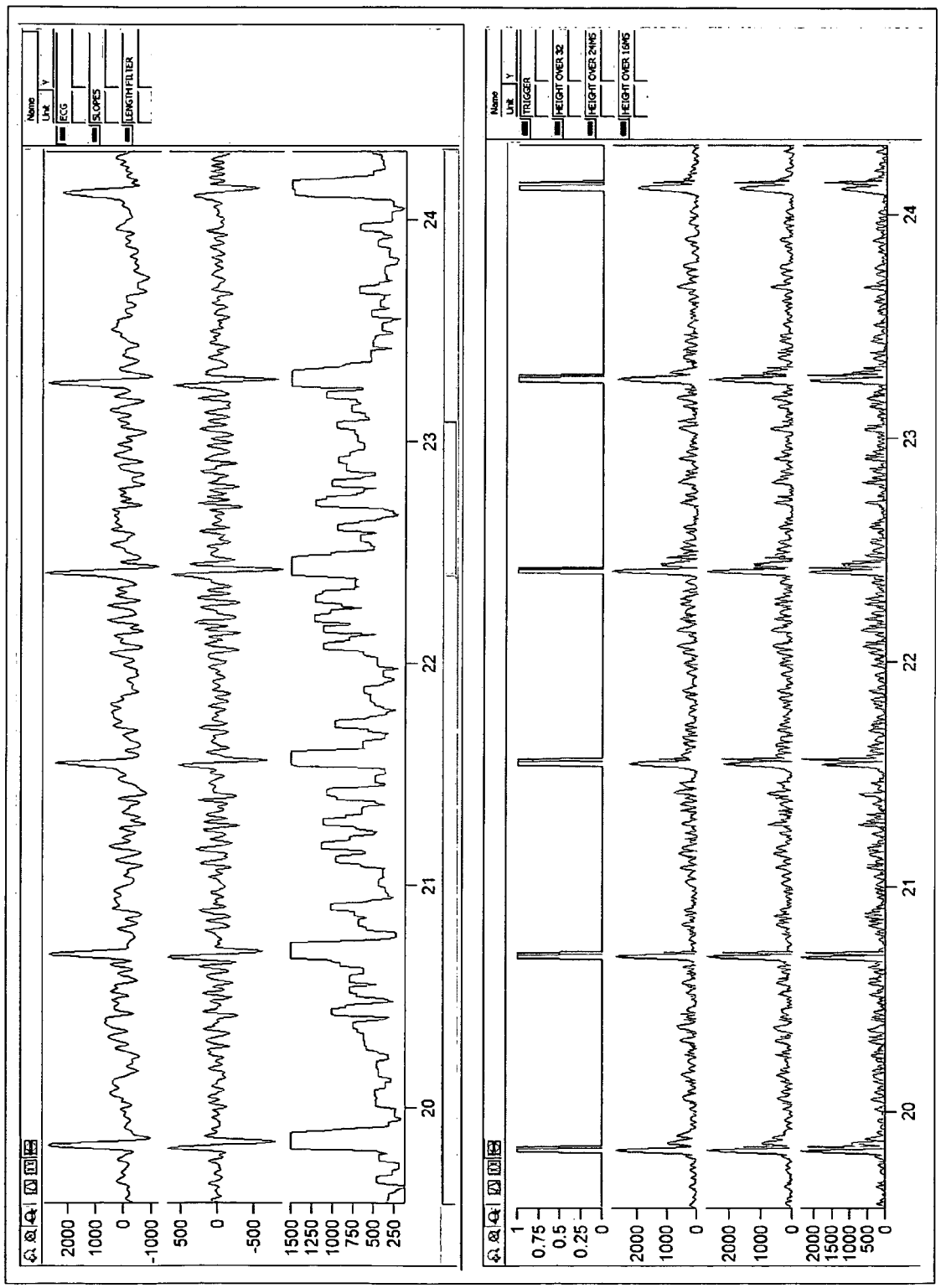
FIG. 5. R wave triggering during skeletal muscle noise on the ECG. The threshold actively adapts to electromyographic (EMG) noise from skeletal muscles by increasing the threshold level to prevent the occurrence of a false trigger.

As shown in FIGS. 1-5, the results and apparatus disclosed herein provide correct triggering on the leading edge of the R wave during periods of normal ECG signals and wide ECG signals, as well as during periods of 60 Hz noise from electrical apparatus and during electromyographic (EMG) noise from skeletal muscles. FIG. 1 shows R wave triggering during different ECG morphologies. The wide ECG shapes shown on the right hand side of the figure can occur during premature ventricular contraction. FIG. 2 illustrates how the threshold for R wave triggering quickly adapts to changes in the noise level on the ECG signal. FIGS. 3 and 4 show correct R wave triggering during periods where the ECG signal is contaminated with 60 Hz noise such as occurs from pickup from electrical apparatus. FIG. 5 shows that the threshold for R wave triggering actively adapts to electromyographic (EMG) noise from skeletal muscle by increasing the threshold level to prevent the occurrence of a false trigger.

Use of the adaptive trigger threshold of the present invention allows a lower initial threshold to be utilized to allow better detection of wide or slow R waves while not increasing the false trigger rate. Noise immunity is also improved because noise and artifacts tend to be bipolar or random, while the R wave trigger described herein is based on unipolar trigger recognition. The present invention does not require convention signal filtering, which causes signal delays, to reliably trigger on the ECG. This is especially beneficial in times of an arrhythmia when rapid and accurate triggering of the IABP from the ECG is important.

REFERENCES

Baskett R J, Ghali W A, Maitland A, Hirsch G M. The intraaortic balloon pump in cardiac surgery. Ann. Thorac. Surg. 74(4):1276-87, 2002.

Kern, M, Aguirre, F, Caracciolo, E, Bach, R, Donohue, T, Lasorda, D, Ohman, M, Schnitzler, R, King, D, Ohley, W, Grayzel, J. Hemodynamic effects of new intra-aortic balloon counterpulsation timing method in patients: A multicenter evaluation. American Heart Journal 137:1129-6, 1999.

Mehlhorn U, Kroner A, de Vivie E R. 30 years clinical intraaortic balloon pumping: facts and figures. Thorac. Cardiovasc. Surg. 47 Suppl 2:298-303, 1999.

Ohley, W J, Nigroni, P, Williams, J, Sarras, L, Hamilton, R. Intraaortic balloon pump response to arrhythmias: Development and implementation of algorithms. Cardioangiology 51(5): 483-7, 2002.

Sakamoto, T, Arai, H, Toshiyuki, M, Suzuki, A. A new algorithm of intra aortic balloon pumping in patients with atrial fibrillation. ASAIO Journal 41:79-83, 1995.

U.S. Pat. No. 4,571,547, Adaptive signal detection system especially for physiological signals such as the R waves of ECG signals, which is desensitized to artifacts, Day, issued Feb. 18, 1986.

U.S. Pat. No. 4,692,148, Intra-aortic balloon pump apparatus and method of using same, Kantrowitz et al., issued Sep. 8, 1987.

U.S. Pat. No. 4,809,681, Electrocardiographic measurement method for controlling an intra-aortic balloon pump, Kantrowitz et al., issued Mar. 7, 1989.

U.S. Pat. No. 5,355,891, ECG analyzer, Wateridge et al., issued Oct. 18, 1994.

U.S. Pat. No. 6,258,035, Device for determining a characteristic point in the cardiac cycle, Hoeksel et al., issued Jul. 10, 2001.

U.S. Pat. No. 6,290,641, Intra-aortic balloon pump having improved automated electrocardiogram based intra-aortic balloon deflation timing, Nigroni et al., issued Sep. 18, 2001.

U.S. Pat. No. 6,569,103, Device for determining a characteristic point in the cardiac cycle, Hoeksel et al., issued May 27, 2003.

U.S. Pat. No. 6,679,829, Intra-aortic balloon pump having improved automated electrocardiogram based intra-aortic balloon deflation timing, Nigroni et al., issued Jan. 20, 2004.

U.S. Pat. No. 6,887,206, Device for determining a characteristic point in the cardiac cycle, Hoeksel et al., issued May 3, 2005.

U.S. patent application Publication No. 2004/0059183, Apparatus for controlling heart assist devices, Jansen et al., published Mar. 25, 2004.

U.S. patent application Publication No. 2005/0148812, Timing of intra-aortic balloon pump therapy, Nigroni et al., published Jul. 7, 2005.

What is claimed is:

1. A method of generating a trigger from an R wave of an electrocardiogram (ECG) waveform using a threshold that adapts to the slope of the R wave during a leading edge of the R wave, the method comprising using a processing unit for:
   a) setting a threshold for the trigger, where the threshold is a percentage of the amplitude of the expected R wave;
   b) measuring slopes of the R wave over successive small time periods during the leading edge of the R wave; where slopes corresponding to waveforms that include frequencies greater than the expected R wave prevent generation of a trigger;
   c) adjusting the threshold for the trigger for the R wave during the leading edge of the R wave, where the threshold is increased if the slopes measured in b) are greater than expected for the R wave;
   d) applying a scalar value to the slopes measured in b) to set a frequency above which signal frequencies are not considered valid for recognition as an R wave; and
   e) generating a trigger during the leading edge of the R wave when the amplitude of the R wave reaches the threshold.

2. The method of claim 1, wherein the amplitude of the expected R wave is normalized based on preceding R waves recorded from the same subject.

3. The method of claim 2, wherein more recently occurring R waves are weighted more heavily in determining the amplitude of the expected R wave than less recently occurring R waves.

4. The method of claim 1, wherein the threshold in step a) is set at $\frac{1}{3}^{rd}$ of the amplitude of the expected R wave.

5. The method of claim 1, wherein the threshold in step a) is set at $\frac{1}{2}$ of the amplitude of the expected R wave.

6. The method of claim 1, wherein individual time periods in step b) are 1 msec to 5 msec in duration.

7. The method of claim 1, wherein individual time periods in step b) are at least 4 msec in duration.

8. The method of claim 1, wherein the successive time periods in step b) have a total duration of 16-40 msec.

9. The method of claim 1, wherein slopes corresponding to waveforms that predominately have frequencies greater than or equal to 40 Hz are excluded from generating a trigger.

10. The method of claim 1, wherein slopes corresponding to waveforms that predominately have frequencies greater than or equal to 30 Hz are excluded from generating a trigger.

11. The method of claim 1, wherein the adjusted threshold is not allowed to exceed a maximum percentage of the amplitude of the expected R wave.

12. The method of claim 1, wherein the adjusted threshold is not allowed to exceed $\frac{2}{3}^{rd}$ of the amplitude of the expected R wave.

13. The method of claim 1, which further comprises excluding slopes corresponding to waveforms that predominately have frequencies less than or equal to 5 Hz from generating a trigger.

14. The method of claim 1, which further comprises excluding slopes corresponding to waveforms that predominately have frequencies less than or equal to 10 Hz from generating a trigger.

15. The method of claim 1, which further comprises requiring that a minimum number of changes in amplitude of the R wave measured over successive time periods in step b) are in the same direction of change in order to generate a trigger.

16. The method of claim 1, which further comprises requiring that a change in amplitude of the R wave measured over a time period of the successive small time periods in step b) has a minimum change with respect to the change in amplitude measured over a preceding time period of the successive small time periods in order to generate a trigger.

17. The method of claim 1, which further comprises increasing the threshold for the trigger in the presence of ECG Signals having a frequency component in the higher range expected for the R wave.

18. The method of claim 1, which further comprises triggering an intra-aortic balloon pump (IABP) by the trigger generated during the leading edge of the R wave in step e).

19. The method of claim 1, which further comprises triggering deflation of an intra-aortic balloon (IAB) by an intra-aortic balloon pump (IABP) by the trigger generated during the leading edge of the R wave in step e).

20. The method of claim 1, which further comprises triggering a cardiac device by the trigger generated during the leading edge of the R wave in step e).

21. The method of claim 20, wherein the cardiac device is a cardiac stimulator, a defibrillator, or an ECG monitor.

22. An apparatus for generating a trigger from an R wave of an electrocardiogram (ECG) waveform using a threshold that adapts to the slope of the R wave during a leading edge of the R wave, the apparatus comprising a processing unit for:
   a) setting a threshold for the trigger, where the threshold is a percentage of the amplitude of the expected R wave;
   b) measuring slopes of the R wave over successive small time periods during the leading edge of the R wave, where slopes corresponding to waveforms that include frequencies greater than the expected R wave prevent generation of a trigger;
   c) adjusting the threshold for the trigger for the R wave during the leading edge of the R wave, where the threshold is increased if the slopes measured in b) are greater than expected for the R wave;
   d) applying a scalar value to the slopes measured in b) to set a frequency above which signal frequencies are not considered valid for recognition as an R wave; and
   e) generating a trigger during the leading edge of the R wave when the amplitude of the R wave reaches the threshold.

23. The apparatus of claim 22, wherein the apparatus comprises an input from the electrocardiogram (ECG) of a subject.

24. The apparatus of claim 23, wherein the apparatus comprises an input from the subject's arterial pressure.

25. The apparatus of claim 22, wherein the apparatus comprises a processing unit for detecting cardiac arrhythmia from a subject's electrocardiogram (ECG) and/or from a subject's arterial pressure.

26. The apparatus of claim 22, wherein the amplitude of the expected R wave is normalized based on preceding R waves in the ECG.

27. The apparatus of claim 26, wherein more recently occurring R waves are weighted more heavily in determining the amplitude of the expected R wave than less recently occurring R waves.

28. The apparatus of claim 22, wherein the threshold in a) is set at $\frac{1}{3}$rd of the amplitude of the expected R wave.

29. The apparatus of claim 22, wherein the threshold in a) is set at $\frac{1}{2}$ of the amplitude of the expected R wave.

30. The apparatus of claim 22, wherein individual time periods in b) are 1 msec to 5 msec in duration.

31. The apparatus of claim 22, wherein individual time periods in b) are at least 4 msec in duration.

32. The apparatus of claim 22, wherein the successive time periods in b) have a total duration of 16-40 msec.

33. The apparatus of claim 22, wherein slopes corresponding to waveforms that predominately have frequencies greater than or equal to 40 Hz are excluded from generating a trigger.

34. The apparatus of claim 22, wherein slopes corresponding to waveforms that predominately have frequencies greater than or equal to 30 Hz are excluded from generating a trigger.

35. The apparatus of claim 22, wherein the adjusted threshold is not allowed to exceed a maximum percentage of the amplitude of the expected R wave.

36. The apparatus of claim 22, wherein the adjusted threshold is not allowed to exceed $\frac{2}{3}^{rd}$ of the amplitude of the expected R wave.

37. The apparatus of claim 22, wherein the processing unit excludes slopes corresponding to waveforms that predominately have frequencies less than or equal to 5 Hz from generating a trigger.

38. The apparatus of claim 22, wherein the processing unit excludes slopes corresponding to waveforms that predominately have frequencies less than or equal to 10 Hz from generating a trigger.

39. The apparatus of claim 22, wherein the processing unit requires that a minimum number of changes in amplitude of the R wave measured over successive time periods in step b) are in the same direction of change in order to generate a trigger.

40. The apparatus of claim 22, wherein the processing unit requires that a change in amplitude of the R wave measured over a time period of the successive small time periods in step b) has a minimum change with respect to the change in amplitude measured over a preceding time period of the successive small time periods in order to generate a trigger.

41. The apparatus of claim 22, wherein the processing unit increases the threshold for the trigger in the presence of ECG signals having a frequency component in the higher range expected for the R wave.

42. The apparatus of claim 22, wherein the apparatus comprises an output that triggers an intra-aortic balloon pump (IABP).

43. The apparatus of claim 22, wherein the apparatus comprises an output that triggers deflation of an intra-aortic balloon (IAB) by an intra-aortic balloon pump (IABP).

44. The apparatus of claim 22, wherein the apparatus is incorporated in an intra-aortic balloon pump console system.

* * * * *